United States Patent [19]

Hu

[11] Patent Number: 5,606,585
[45] Date of Patent: Feb. 25, 1997

[54] METHODS AND APPARATUS FOR MULTISLICE HELICAL IMAGE RECONSTRUCTION IN A COMPUTER TOMOGRAPHY SYSTEM

[75] Inventor: Hui Hu, Waukesha, Wis.

[73] Assignee: General Electric Company, Milwaukee, Wis.

[21] Appl. No.: 576,765

[22] Filed: Dec. 21, 1995

[51] Int. Cl.$^6$ ........................................ A61B 6/03
[52] U.S. Cl. ................................. 378/15; 378/901
[58] Field of Search .................. 364/413, 17; 378/15, 378/901

[56] References Cited

U.S. PATENT DOCUMENTS

| | | | |
|---|---|---|---|
| 4,580,219 | 4/1986 | Pelc et al. | 364/413.21 |
| 4,821,210 | 4/1989 | Rumbaugh | 395/121 |
| 5,047,931 | 9/1991 | Lin | 364/413.21 |
| 5,233,518 | 8/1993 | King et al. | 364/413.18 |
| 5,253,171 | 10/1993 | Hsiao et al. | 364/413.19 |
| 5,265,142 | 11/1993 | Hsieh | 378/4 |
| 5,270,923 | 12/1993 | King et al. | 364/413.13 |
| 5,406,479 | 4/1995 | Harman | 364/413.17 |
| 5,469,486 | 11/1995 | Hu et al. | 378/4 |
| 5,469,487 | 11/1995 | Hu | 378/9 |
| 5,491,735 | 2/1996 | Hsieh | 378/15 |

OTHER PUBLICATIONS

Crawford et al., "Computed tomography scanning with simultaneous patient translation", *Medical Physics*, vol. 17, No. 6, Nov./Dec. 1990, pp. 967–982.

*Primary Examiner*—David P. Porta
*Assistant Examiner*—David Vernon Bruce
*Attorney, Agent, or Firm*—John S. Beulick; John H. Pilarski

[57] ABSTRACT

The present invention, in one form, is a method for performing image reconstruction from projection data acquired in a multislice helical scan. More specifically, a helical weighting factors is generated and then a modified weighting factor $\hat{W}m(\beta,\gamma)$, which is a shifted and weighted average version of the helical weighting factor, is generated. The modified weighting factor is then applied to projection data.

16 Claims, 1 Drawing Sheet

METHODS AND APPARATUS FOR MULTISLICE HELICAL IMAGE RECONSTRUCTION IN A COMPUTER TOMOGRAPHY SYSTEM

FIELD OF THE INVENTION

This invention relates generally to computed tomography (CT) imaging and more particularly, to image reconstruction in a multislice CT system.

SUMMARY OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighting ("HW") algorithms which weight the collected data as a function of view angle and detector channel index. Specifically, prior to filtered back projection, the data is weighted according to a helical weighting factor, which is a function of both the gantry angle and detector angle. Although the known algorithms generate compact slice profiles, some noticeable artifacts may be generated in the reconstructed image.

It would be desirable to provide an algorithm which facilitates the reduction of artifacts and offers reasonable trade-offs between artifact reduction and slice profile in helical image reconstruction. It also would be desirable to provide such an algorithm which does not significantly increase the processing time.

SUMMARY OF THE INVENTION

These and other objects may be attained in a system which, in one embodiment, includes a projection domain z smoothing algorithm that generates a modified weighting factor. More particularly, and in accordance with one embodiment of the present invention, a helical reconstruction algorithm weighting factor is shifted in the view angle direction and weighted to generate the modified weighting factor in a multislice CT system. As used herein, the term "multislice CT system" typically refers to a CT system having a detector array with more than one, e.g., two or four, rows of detector cells. Of course, more or fewer detector cell rows may be used. An example of an image reconstruction algorithm which may be utilized in reconstructing an image from data obtained in a helical scan is described in U.S. patent application Ser. No. 08/436,176, filed May 9, 1995, and assigned to the present assignee.

Specifically, and in accordance with one embodiment, the helical weighting factor is modified according to gantry angle ($\beta$) and detector angle ($\gamma$) in accordance with the following:

$$\hat{W}m(\beta,\gamma) = \sum_{i=-n}^{i=n} h(i) Wm(\beta - i\Delta\beta, \gamma)$$

where:

$\gamma$ is the detector angle;

$\beta$ is the gantry angle;

m is the detector row index;

$Wm(\beta,\gamma)$ is the original weighting coefficient generated by the helical reconstruction algorithm;

$\Delta\beta$ is the shift along the view angle direction; and $h(i)$ is the weighting applied to the i th shifted version. The modified weighting factor is thus a shifted and weighted average version of the original weighting factor for each view angle and gantry angle.

By modifying the weighting factor as described above, the reduction of artifacts in multislice helical image reconstruction may be achieved. Such algorithm also does not significantly increase the processing time and offers reasonable trade-offs between artifact reduction and slice profile.

DETAILED DESCRIPTION OF THE DRAWINGS

Figure 1:
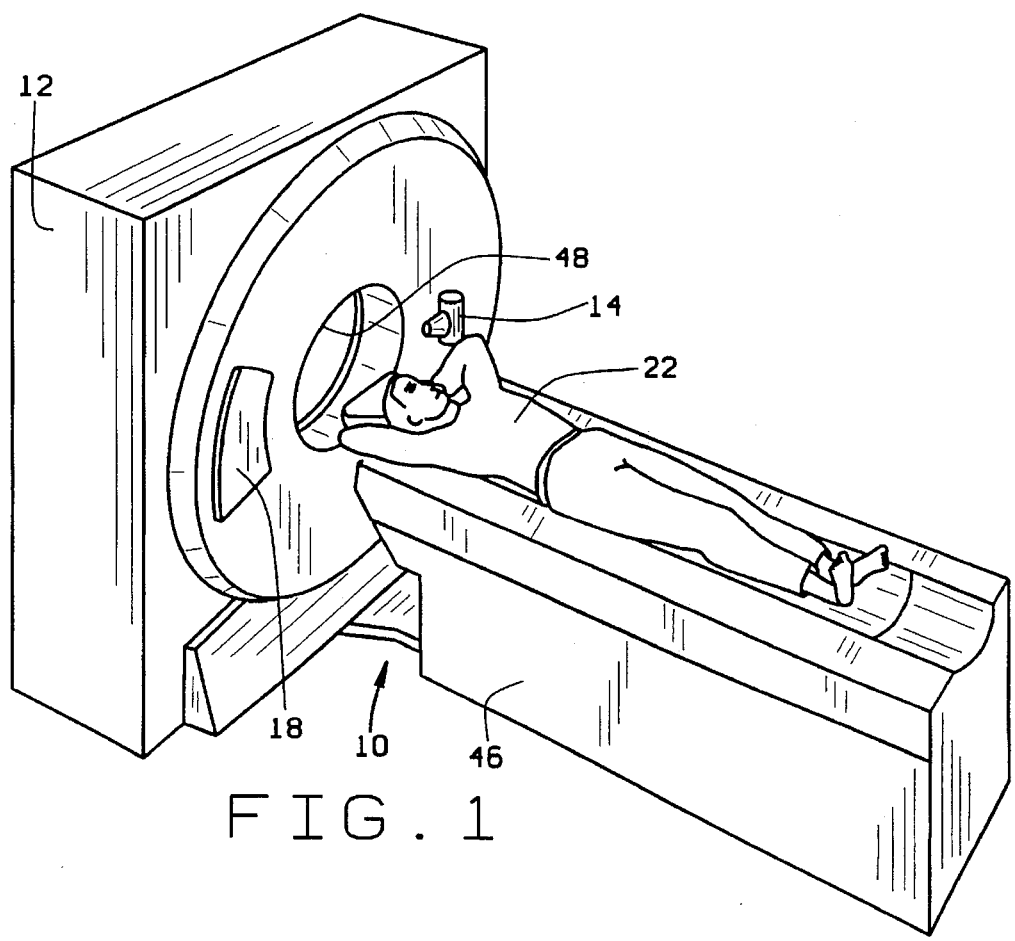
FIG. 1 is a pictorial view of a CT imaging system.
Figure 2:
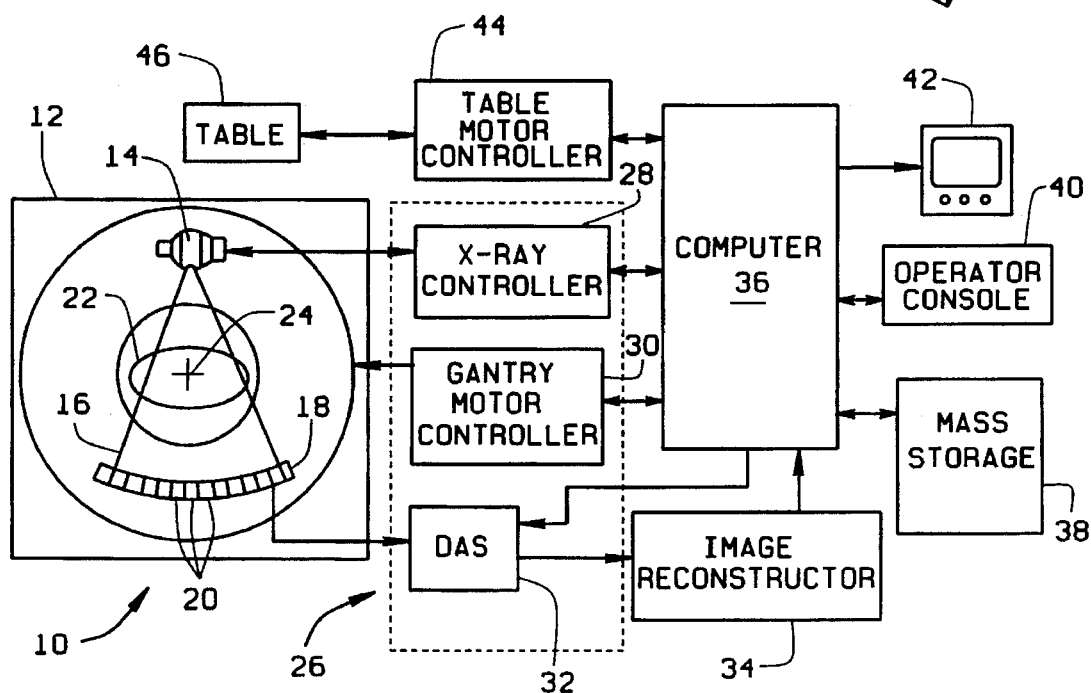
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on both the fan angle and view angle.

The following discussion of a z smoothing algorithm and image quality sometimes refers specifically to multislice CT scanners, which typically include detector arrays have two to four rows of detector cells. The z smoothing algorithm, however, is not limited to practice in connection with only two and four slice scanners and may be used with other CT scanners. Moreover, the present weighting factor modification is not directed to any particular helical image reconstruction algorithm. Rather, the present weighting factor modification may be used in conjunction with many different types of helical weighting factors. Further, in one embodiment, the z smoothing algorithm would be implemented in computer 36 and would process, for example, data stored in mass storage 38. Many other alternative implementations are, of course, possible.

As one specific example, in a multi slice system with m rows of detectors, if a helical reconstruction algorithm is to be applied to projection data during reconstruction, and the weighting factor accorded to each gantry angle ($\beta$) and detector angle ($\gamma$) is $Wm(\beta,\gamma)$. In accordance with the present invention, the modified weighting factor $\hat{W}m(\beta,\gamma)$ is:

$$\hat{W}m(\beta,\gamma) = \sum_{i=-n}^{i=n} h(i)Wm(\beta - i\Delta\beta, \gamma)$$

where:
$\gamma$ is the detector angle;
$\beta$ is the gantry angle;
m is the detector row index;
$Wm(\beta,\gamma)$ is the weighting coefficient, applied or pursuant to, a helical reconstruction algorithm;
$\Delta\beta$ is the shift along the view angle direction; and
h(i) is the weighting applied to the i th shifted version.
This modified weighting factor $\hat{W}m(\beta,\gamma)$ is a shifted and weighted average version of the helical weighting function. A total of 2n+1 terms is averaged. The modified weighting factor $\hat{W}m(\beta,\gamma)$ is then applied to the projection data.

Known multislice scanners typically have multiple rows of detectors 20 per slice. For example, a two slice detector has two rows of detectors 20, and a four slice detector has four rows of detectors 20. Accordingly, the helical weighting applied to projection data collected by detectors 20 is dependent upon the detector row index from which the data is obtained. Therefore, the weighting factor $\hat{W}m(\beta,\gamma)$ is also dependent upon detector row index, m.

The profile width of the resulting z-averaged slice is related to both the intrinsic slice profile, i.e., the original slice profile without any z smoothing, and the smoothing region. The smoothing region is represented by $2n\Delta\beta$. The detailed shape of the profile of the resulting slice is also affected by kernel h(i), which is normalized to one.

In accordance with one embodiment, n, $\Delta\beta$ and h(i) are selected in the final stage of image quality evaluation. Accordingly, these values may be inserted by an operator at console 40 or may be stored in computer 36. In one embodiment, if the width of profile of the z-smoothed slice will not be larger than twice the intrinsic width, then it is believed that $n \leq 5$ is sufficient to remove image artifacts resulting from helical scanning. The load for computing $\hat{W}m(\beta,\gamma)$ is only (2n+1)t+(2n+1) multiples+2n additions, where t is the load for computing the original weighting function $Wm(\beta,\gamma)$.

The above described algorithm facilitates reducing artifacts in multislice helical image reconstruction. Such algorithm also does not significantly increase the processing time and offers reasonable trade-offs between artifact reduction and slice profile.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while the values on n, $\Delta\beta$ and h(i) are described herein being selected as the final stage of image quality evaluation, any or all of these values may be pre-selected and stored in the computer. Moreover, while the description herein references two and four slice scanners, the present algorithm may be used in connection with other slice scanners. Accordingly, the spirit and scope of the invention are to be limited only by the terms of the appended claims.

What is claimed is:

1. A system for producing a tomographic image of an object using projection data acquired in a multislice helical scan, said system comprising a detector array comprising a plurality of rows of detectors, said system configured to:

identify a modified weighting factor based on a helical weighting factor, the helical weighting factor based on gantry angle and detector angle, and the modified weighting factor identified by shifting the helical weighting factor in the view angle direction and being dependent upon a detector row index; and apply the identified modified weighting factor to the projection data.

2. A system in accordance with claim 1 wherein said modified weighting factor $\hat{W}m(\beta,\gamma)$ is:

$$\hat{W}m(\beta,\gamma) = \sum_{i=-n}^{i=n} h(i)Wm(\beta - i\Delta\beta,\gamma)$$

where:

γ is the detector angle;

β is the gantry angle;

m is the detector row index;

Wm(β,γ) is the helical weighting coefficient;

Δβ is the shift along the view angle direction; and h(i) is the weighting applied to the i th shifted version.

3. A system in accordance with claim 2 wherein n≦5.

4. A system in accordance with claim 2 wherein n, Δβ and i are selected in the final stage of an image quality evaluation.

5. A system in accordance with claim 2 wherein said system further comprises a computer having a memory, values for n, Δβ and i being stored in said memory.

6. A system in accordance with claim 2 wherein said system further comprises a console for receiving inputs regarding n, Δβ and i.

7. A method for generating a modified weighting factor to be utilized in weighting projection data acquired in a multislice helical scan, said method comprising the steps of:

identifying a modified weighting factor based on a helical weighting factor, the helical weighting factor based on gantry angle and detector angle, and identifying the modified weighting factor comprising the step of shifting the helical weighting factor in the view angle direction, the modified weighting factor being dependent upon a detector row index; and applying the modified weighting factor to the projection data.

8. A method in accordance with claim 7 wherein the modified weighting factor $\hat{W}m(\beta,\gamma)$ is:

$$\hat{W}m(\beta,\gamma) = \sum_{i=-n}^{i=n} h(i)Wm(\beta - i\Delta\beta,\gamma)$$

where:

γ is the detector angle;

β is the gantry angle;

m is the detector row index;

Wm(β,γ) is the helical weighting coefficient;

Δβ is the shift along the view angle direction; and h(i) is the weighting applied to the i th shifted version.

9. A method in accordance with claim 8 wherein n≦5.

10. A method in accordance with claim 8 wherein n, Δβ and i are selected in the final stage of an image quality evaluation.

11. A method in accordance with claim 8 wherein values for n, Δβ and i being stored in a computer memory of a computer programmed to perform image reconstruction.

12. Apparatus for producing a tomographic image of an object using projection data acquired in a multislice helical scan, said apparatus comprising:

a detector array comprising a plurality of rows of detectors;

a computer coupled to said detector array, said computer programmed to:

identify a modified weighting factor based on a helical weighting factor, the helical weighting factor based on gantry angle and detector angle, and the modified weighting factor identified by shifting the helical weighting factor in the view angle direction and being dependent upon a detector row index; and apply the identified modified weighting factor to the projection data.

13. Apparatus in accordance with claim 12 wherein said modified weighting factor $\hat{W}m(\beta,\gamma)$ is:

$$\hat{W}m(\beta,\gamma) = \sum_{i=-n}^{i=n} h(i)Wm(\beta - i\Delta\beta,\gamma)$$

where:

γ is the detector angle;

β is the gantry angle;

m is the detector row index;

Wm(β,γ) is the helical weighting coefficient;

Δβ is the shift along the view angle direction; and h(i) is the weighting applied to the i th shifted version.

14. Apparatus in accordance with claim 13 wherein n≦5.

15. Apparatus in accordance with claim 13 wherein n, Δβ and i are selected in the final stage of an image quality evaluation.

16. Apparatus in accordance with claim 13 wherein said computer comprises a memory, values for n, Δβ and i being stored in said memory.

* * * * *